(12) United States Patent
Tang et al.

(10) Patent No.: US 8,165,654 B2
(45) Date of Patent: Apr. 24, 2012

(54) TEXTILE STRUCTURE FOR DETECTING BODY SURFACE ELECTRICAL SIGNALS OF HUMAN AND SIGNAL DETECTOR USING THE SAME

(75) Inventors: Chien-Fa Tang, Taipei Hsien (TW); Chien-Lung Shen, Chiayi (TW); Kun-Chuan Tsai, Taipei County (TW)

(73) Assignee: Taiwan Textile Research Institute, New Taipei (TW)

( * ) Notice: Subject to any disclaimer, the term of this patent is extended or adjusted under 35 U.S.C. 154(b) by 1122 days.

(21) Appl. No.: 12/022,121

(22) Filed: Jan. 29, 2008

(65) Prior Publication Data

US 2008/0183063 A1 Jul. 31, 2008

(30) Foreign Application Priority Data

Jan. 30, 2007 (TW) ................................ 96103366 A

(51) Int. Cl.
*A61B 5/04* (2006.01)
(52) U.S. Cl. ......... 600/388; 600/386; 600/384; 600/382
(58) Field of Classification Search .................. 600/384, 600/386, 388–393, 484, 536, 513
See application file for complete search history.

(56) References Cited

U.S. PATENT DOCUMENTS

| | | |
|---|---|---|
| 4,807,640 A | 2/1989 | Watson et al. |
| 4,815,473 A | 3/1989 | Watson et al. |
| 4,834,109 A | 5/1989 | Watson |
| 5,241,300 A | 8/1993 | Buschmann |
| 5,374,283 A * | 12/1994 | Flick ............................. 607/46 |
| 6,102,856 A | 8/2000 | Groff et al. |
| 6,341,504 B1 | 1/2002 | Istook |
| 6,450,957 B1 | 9/2002 | Yoshimi et al. |
| 6,474,367 B1 | 11/2002 | Jayaraman et al. |
| 6,537,228 B1 | 3/2003 | Lambert |
| 6,551,252 B2 | 4/2003 | Sackner et al. |
| 6,687,523 B1 | 2/2004 | Jayaramen et al. |
| 6,778,090 B2 | 8/2004 | Newham |
| 6,783,498 B2 | 8/2004 | Sackner et al. |
| 7,966,052 B2 * | 6/2011 | DeFusco et al. .............. 600/386 |
| 2003/0212319 A1 * | 11/2003 | Magill .......................... 600/382 |
| 2005/0054941 A1 * | 3/2005 | Ting et al. .................... 600/529 |

FOREIGN PATENT DOCUMENTS

WO WO 2004100784 A2 * 11/2004
* cited by examiner

*Primary Examiner* — Linda Dvorak
*Assistant Examiner* — Brian M Antiskay
(74) *Attorney, Agent, or Firm* — Jianq Chyun IP Office

(57) ABSTRACT

A textile structure for detecting body surface electrical signals of human is provided. The textile structure includes a non-conductive textile, a conductive textile, and a plurality of test terminals. The non-conductive textile covers the human body. The conductive textile has a first region, a second region, and a third region. The first region is interdigitated into but not electrically coupled to the third region. The first to third test terminals are respectively coupled to the first to third regions of the conductive textile. The first and second test terminals are used for detecting ECG signals. The first and third test terminals are used for detecting respiratory signals.

8 Claims, 5 Drawing Sheets

TEXTILE STRUCTURE FOR DETECTING BODY SURFACE ELECTRICAL SIGNALS OF HUMAN AND SIGNAL DETECTOR USING THE SAME

CROSS-REFERENCE TO RELATED APPLICATION

This application claims the priority benefit of Taiwan application serial no. 96103366, filed on Jan. 30, 2007. The entirety of the above-mentioned patent application is hereby incorporated by reference herein and made a part of this specification.

BACKGROUND OF THE INVENTION

1. Field of the Invention

The present invention generally relates to a textile structure for detecting body surface electrical signals of human and a signal detector using the same.

2. Description of Related Art

Currently, sensing devices have been used to detect body surface electrical signals of human (such as ECG signals representing heartbeat). In the past, textile structures of metal lines and optical fibre are used to detect the body surface electrical signals of human. However, the optical fibre conversion circuit is difficult to design, and the self inductance of the metal lines is likely to be interfered by external magnetic fields. Furthermore, as the metal lines are contained, such textile structures are stiff and not soft enough, and the degree of refinement of the fibres is limited.

Furthermore, U.S. Pat. No. 4,807,640 discloses a sensing textile structure that performs a respiratory sensing through the electromagnetic self-inductance stretching with the textile structure. Therefore, the sensing textile structure can serve as a respiratory monitor. However, as metal lines are used similarly, the sensing textile structure is stiff and not soft enough.

Furthermore, U.S. Pat. No. 6,537,228 discloses a textile structure applicable to sleep respiratory sensing, activity monitoring apparatus or sudden infant death syndrome (SIDS) apparatus, which detects the body surface electrical signals of human, such as respiratory signals, ECG/heartbeat signals with impedances of patch electrodes.

Now, a textile structure containing conductive yarn and common textile fibres has been developed. The textile structure combined with an electrical loop can serve as a detector for detecting the body surface electrical signals of human. For example, the detector can be used to detect heartbeat signals or respiratory signals respectively.

The textile structure is air permeable, soft, elastic, stretchable, capable of washed with water, and flexible. Therefore, a textile structure having the above advantages and a signal detector using the same are provided preferably, which can be used for detecting the body surface electrical signals of human.

SUMMARY OF THE INVENTION

Accordingly, the present invention is directed to a textile structure for detecting body surface electrical signals of human, which is applicable to measure respiratory signals and heartbeat signals.

The present invention is directed to a signal detector for detecting body surface electrical signals of human, which is applicable to measure respiratory signals and heartbeat signals.

A textile for detecting body surface electrical signals of human is provided, which includes a non-conductive textile, a conductive textile, a first test terminal, a second test terminal, and a third test terminal. The non-conductive textile covers a human body part heaving with breathing. The conductive textile is coupled to the non-conductive textile. The conductive textile has a first region, a second region, and a third region. The first region is interdigitated into but not electrically coupled to the third region. The first to third test terminals are respectively coupled to the first to third regions of the conductive textile. The first and second test terminals are used for detecting ECG signals, and the first and third test terminals are sued for detecting respiratory signals.

A textile structure for detecting body surface electrical signals of human is further provided, which includes a non-conductive textile, a first conductive textile, and a second conductive textile, a first test terminal, a second test terminal, and a third test terminal. The non-conductive textile covers a human body. The first and second conductive textiles are coupled to the non-conductive textile. The first conductive textile has a first region, a second region, and a third region. The first to third test terminals are respectively coupled to the first to third regions of the conductive textile. The second conductive textile is connected to the first region and the second region of the first conductive textile. The conductivity of the first conductive textile is much higher than that of the second conductive textile. The first and second test terminals are used for detecting ECG signals, and the first and third test terminals are used for detecting respiratory signals.

Additionally, a signal detector is further provided, which includes a textile signal acquiring and processing unit and a filter circuit. The textile structure can be one of the two textile structures. The signal acquiring and processing unit is coupled to a plurality of test terminals of the textile structure to acquire and process the body surface electrical signals of human. The filter circuit is coupled to the signal acquiring and processing unit. The filter circuit separates the ECG signals and the respiratory signals from the signals processed by the signal acquiring and processing unit.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
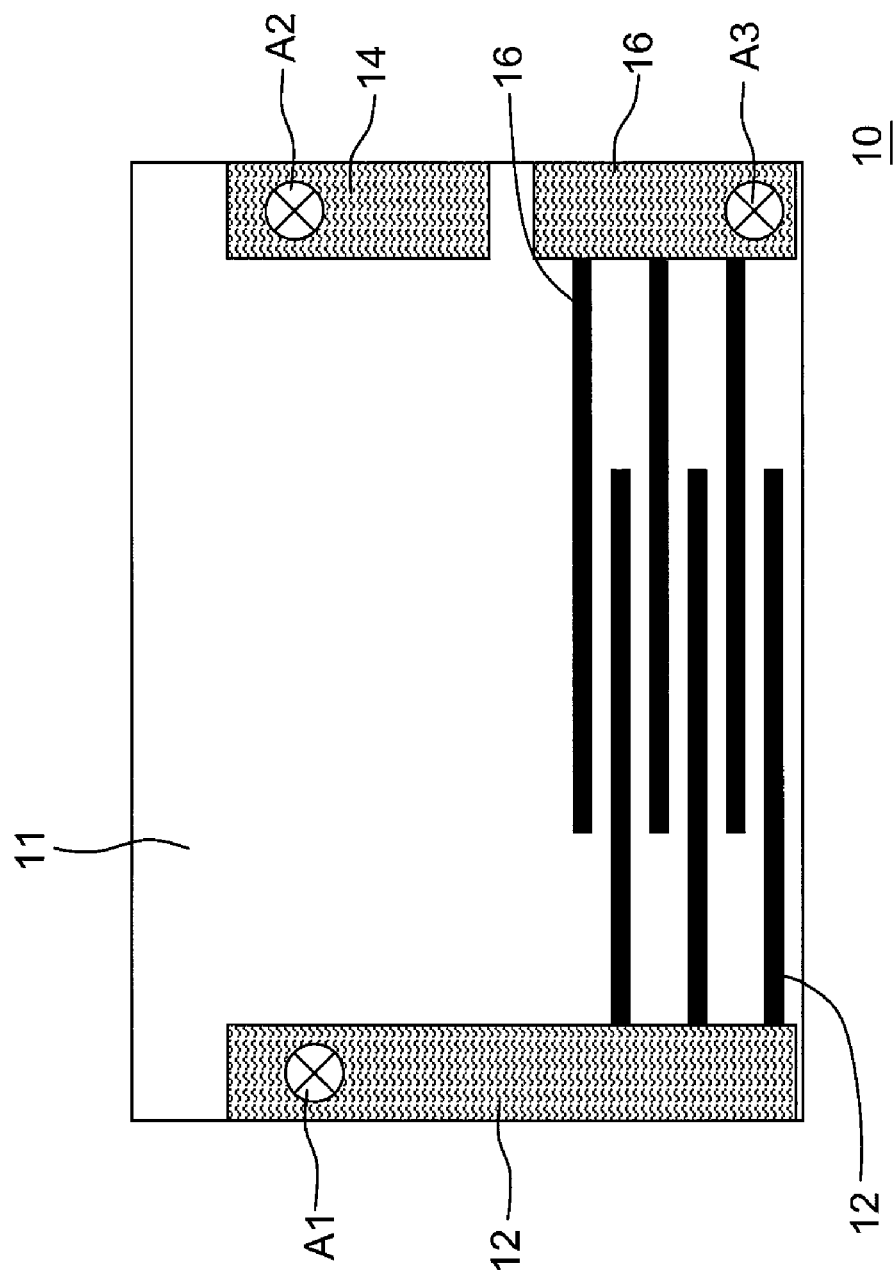
FIGS. 1a and 1b show a textile for detecting body surface electrical signals of human according to a first embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

The embodiments of the present invention provide a textile structure capable of measuring respiratory signals and heartbeat signals and a signal detector using the same.

First Embodiment

Figure 1B:
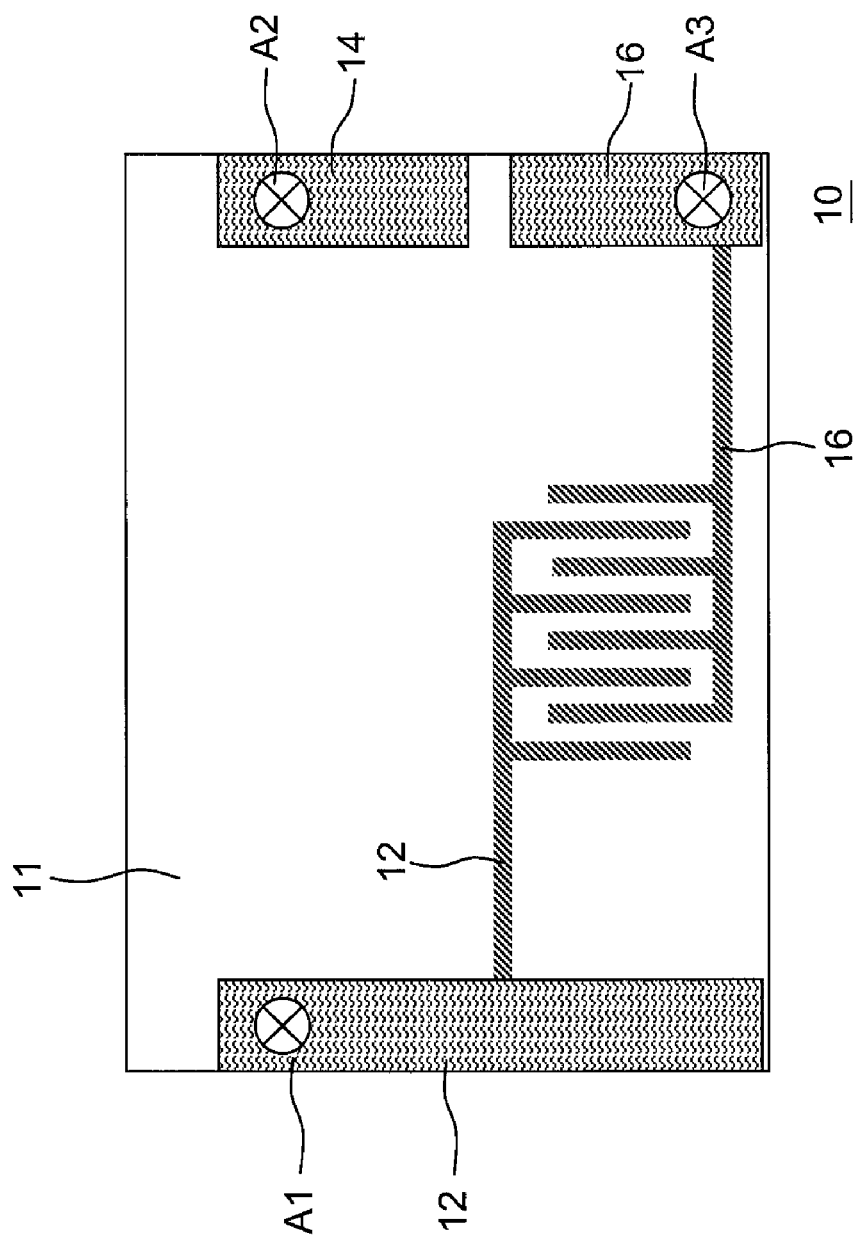

Referring to FIGS. 1a and 1b, a textile structure 10 for detecting body surface electrical signals of human according to a first embodiment of the present invention is shown. The textile 10 includes a non-conductive textile 11, a conductive textile, and test terminals A1-A3.

The non-conductive textile 11 covers the human body. Particularly, the non-conductive textile 11 covers human body parts that heaving with breathing, such as breast and abdomen.

The conductive textile is formed on the non-conductive textile 11. The conductive textile can be divided into three measurement regions, i.e., regions 12, 14, and 16. It should be noted that, the extended parts of the regions 12 and 16 are interdigitated into but not electrically coupled to each other. As shown in FIG. 1a, the extended parts of the regions 12 and 16 are horizontally extended. As shown in FIG. 1b, the extended parts of the regions 12 and 16 are vertically extended. Additionally, the extended parts of the regions 12 and 16 can also be obliquely extended.

The test terminal A1 is coupled to the region 12 of the conductive textile. The test terminal A2 is coupled to the region 14 of the conductive textile. The test terminal A3 is coupled to the region 16 of the conductive textile. The test terminal A1 and the test terminal A2 are used for detecting the ECG signals of human, and the test terminal A3 serves as a signal feedback/reference terminal. The test terminal A1 and test terminal A3 are used for detecting the respiratory signals of human.

The conductive textile and the test terminals can be coupled in various manners, but those skilled in the art should understand that the present invention is not limited to these described.

For example, conductive fibres of the conductive textile and the test terminals can be coupled by pressing and attaching a metal male-female buckle, and then the test terminals are connected to external physical lines by pressing and attaching the metal male-female buckle. That is to say, in such a coupling manner, the test terminals can be implemented as metal male-female buckles.

Alternatively, the test terminals can be implemented as hollow terminals. That is, the conductive fibres and the external physical lines are penetrated into the hollow terminals, and the conductive fibres, the external physical lines, and the hollow terminals are tightly pressed into one piece.

Alternatively, the test terminals can be implemented as conductive glue. The conductive glue is, for example, a high-conductivity polymer epoxy resin. The conductive glue can form a physical electrical interface between the conductive fibres and the external physical lines.

The test terminals A1-A3 and the conductive fibres can be coupled by using one of the above methods, which is unnecessarily to be the same.

Hereinafter, the situation of using the textile 10 to measure heartbeat and breathing is illustrated.

When measuring an ECG signal, the test terminal A1 and the test terminal A2 are used to measure the ECG signal, and the other test terminal A3 serves as the feedback reference terminal of the measured signal to stabilize the signal. The variation of the impedance between the test terminal A1 and the test terminal A2 is used to measure the ECG signal.

When detecting a respiratory signal of human, the test terminal A1 receives an external control signal (not shown). The electrical field of the textile structure 10 varies with the frequency of the external control signal. The test terminal A3 receives the signal sent by the test terminal A1. The textile structure 10 is deformed with the breathing of the human body. That is, the left and right sides of the textile structure 10 are stretched, and the distance between the upper and lower sides gets a little short.

A numerical processing is performed on the signal received by the test terminal A3, so as to calculate the variation of the signal with the respiratory activity of the human body. That is to say, the respiratory activity of the human body can be detected.

Second Embodiment

Figure 2:
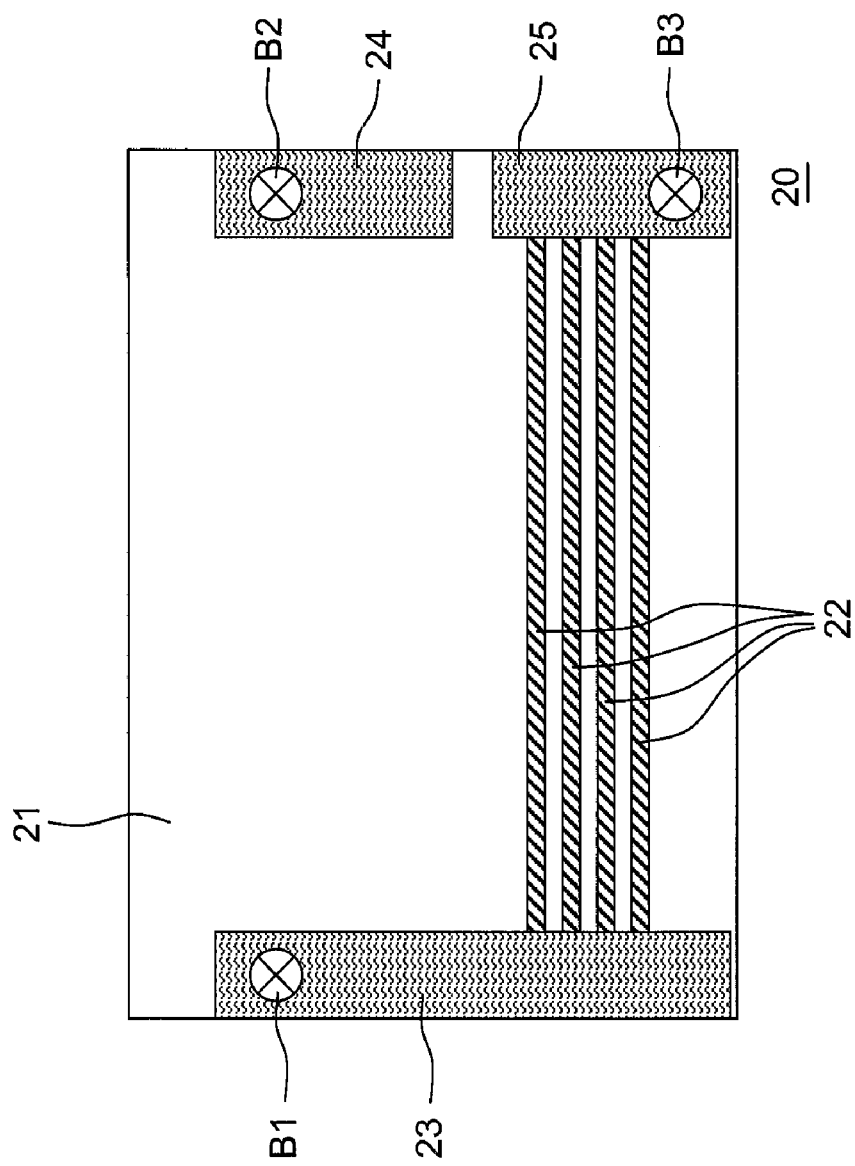
FIG. 2 shows a textile for detecting body surface electrical signals of human according to a second embodiment of the present invention.

Referring to FIG. 2, a textile structure 20 for detecting body surface electrical signals of human according to a second embodiment of the present invention is shown.

As shown in FIG. 2, the textile structure 20 includes a non-conductive textile 21, a good-conductive textile, test terminals B1-B3, and a high-resistance conductive textile 22. The textile structure 20 is formed, for example, by knitting.

The non-conductive textile 21 covers the human body. Particularly, the non-conductive textile 21 covers human body parts that heaving with breathing, such as breast and abdomen.

The good-conductive textile is coupled to the non-conductive textile 21. The coefficient of resistance of the good-conductive textile is less then 50 Ω/cm. The good-conductive textile at least has regions 23, 24, and 25. The test terminal B1 is coupled to the region 23 of the good-conductive textile. The test terminal B2 is coupled to the region 24 of the good-conductive textile. The test terminal B3 is coupled to the region 25 of the good-conductive textile.

The High-resistance conductive textile 22 is coupled to the non-conductive textile 21. The high-resistance conductive textile 22 is connected between the region 23 and the region 25 of the good-conductive textile. The coefficient of resistance of the high-resistance conductive textile 22 is between $10^4$ Ω/cm and $10^6$ Ω/cm. The conductivity of the good-conductive textile is much higher than that of the high-resistance conductive textile 22. The high-resistance conductive textile 22 has another property that the resistance varies with the deformation thereof. Although in FIG. 2, the high-resistance conductive textile 22 covers the abdomen of the human body, the high-resistance conductive textile 22 can also cover the breast of the human body.

The test terminals B1 and B2 are used for detecting the ECG signal. The test terminals B1 and B3 are used for detecting the respiratory signal. The test terminals B1-B3 and the good-conductive textile/high-resistance conductive textile 22 can be coupled in a manner similar to that in the first embodiment and will not be repeated herein.

When measuring the ECG signal, the test terminal B1 and the test terminal B2 are used to measure the ECG signal, and the other test terminal B3 serves as the feedback reference terminal of the measured signal to stabilize the signal. The variation of the impedance between the test terminal B1 and the test terminal B2 is used to measure the ECG signal.

The textile structure 20 is deformed with the breathing of the human body. The left and right sides of the textile structure 20 are stretched, and the distance between the upper and lower sides gets a little short. That is, the high-resistance conductive textile 22 is also deformed. The resistance of the high-resistance conductive textile 22 varies with the deformation thereof. Therefore, by measuring the variation of the resistance between the two test terminals B1 and B3 the respiratory signal of the human body is represented.

Third Embodiment

Figure 3:
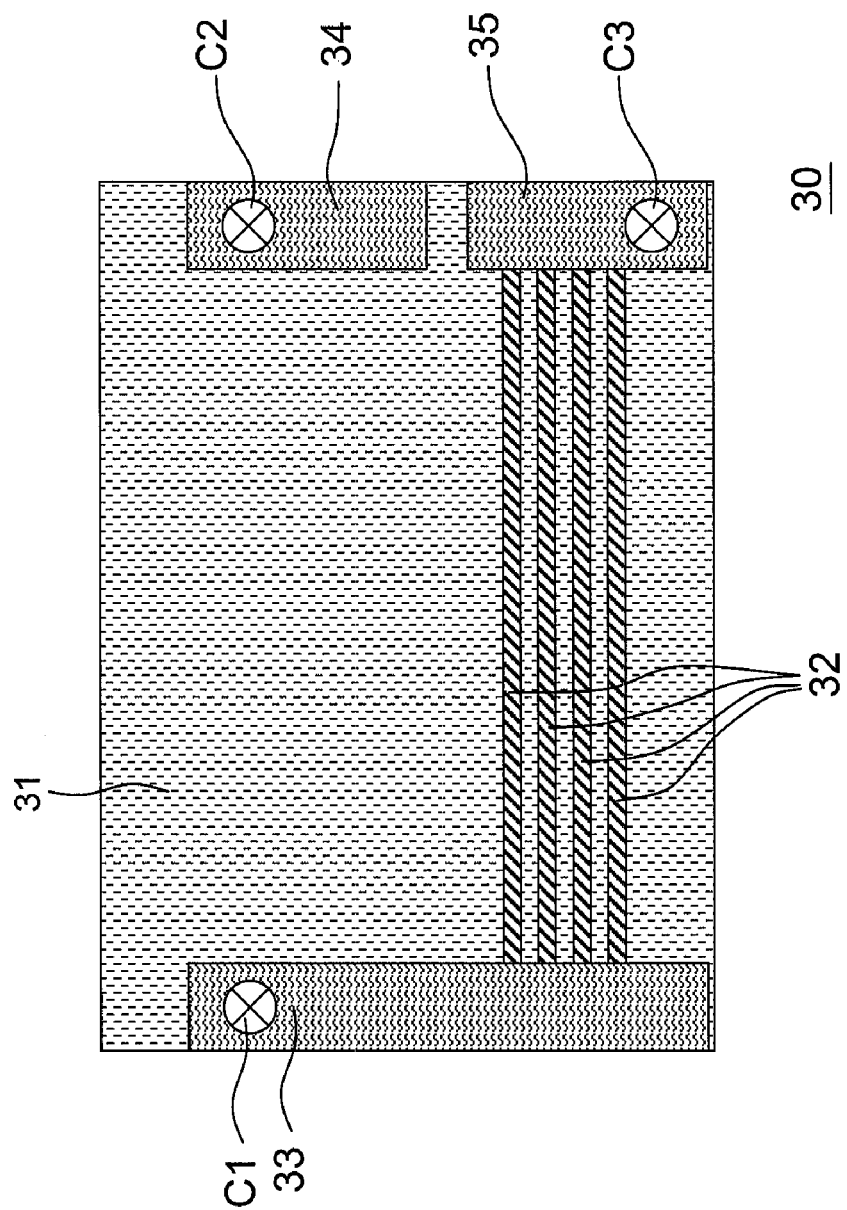
FIG. 3 shows a textile for detecting body surface electrical signals of human according to a third embodiment of the present invention.

Referring to FIG. 3, a textile structure 30 for detecting body surface electrical signals of human according to a third embodiment of the present invention is shown.

As shown in FIG. 3, the textile structure 30 includes a non-conductive textile 31, a good-conductive textile, test terminals C1-C3, and a high-resistance conductive textile 32. The textile structure 30 is formed, for example, by tatting. The good-conductive textile includes regions 33-35.

The composition of the textile structure 30 and the principle of using the same for measuring heartbeat and respiratory signals are substantially similar to those of the textile structure 20 in the second embodiment and will not be repeated herein.

Fourth Embodiment

Figure 4:
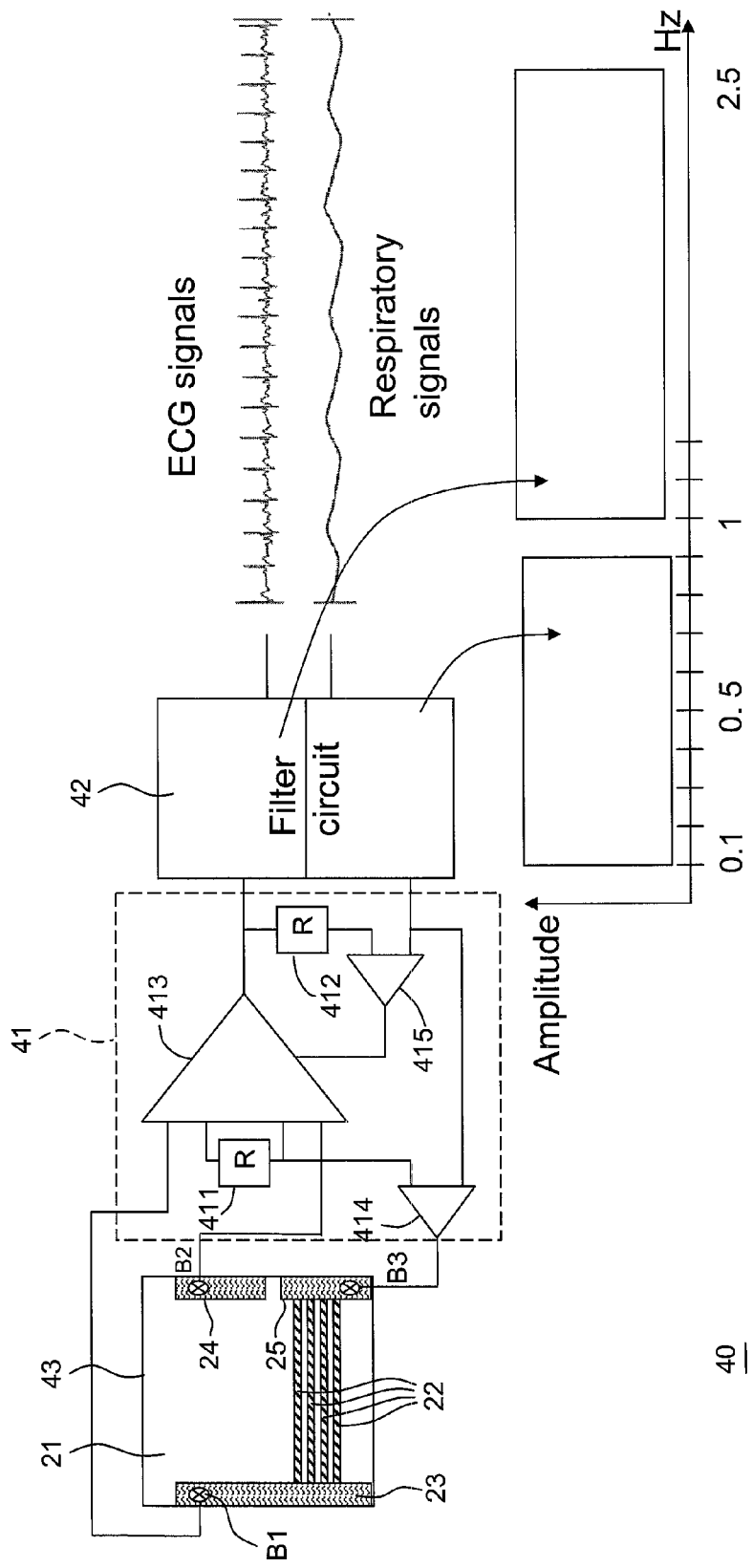
FIG. 4 shows a signal detector for detecting heartbeat and/or respiratory signals according to a fourth embodiment of the present invention.

Referring to FIG. 4, a signal detector 40 for detecting heartbeat and/or respiratory signals according to a fourth embodiment of the present invention is shown. As shown FIG. 4, the signal detector 40 includes a signal acquiring and processing unit 41, a filter circuit 42, and a textile structure 43.

The architecture of the textile structure 43 is similar to that of the textile structures 10-30 in FIGS. 1-3 and will not be repeated herein. In FIG. 4, the textile structure 20 is illustrated as an example.

The signal acquiring and processing unit 41 is coupled to a plurality of test terminals of the textile 40 to acquire and process body surface electrical signals of human sent by the textile structure 43.

The signal acquiring and processing unit 41 includes resistors 411 and 412, and comparators 413-415. The connection between the elements is as shown in FIG. 4 and will not be repeated herein.

The filter circuit 42 is coupled to the signal acquiring and processing unit 41. The filter circuit 42 separates the ECG signal and/or the respiratory signal from the signal processed by the signal acquiring and processing unit 41.

Generally, for infants and adults, the breathing of human is about 8 to 55 times per minute. That is to say, the frequency of the respiratory signal is between 0.133 Hz and 0.9 Hz. The heartbeat of human is about 60 to 200 times per minute. That is to say, the frequency of heartbeat signal is between 1 Hz and 3.3 Hz.

The filter circuit 42 can consider the signal having a frequency between 1 Hz and 3.3 Hz as a heartbeat signal of human and consider the signal having a frequency between 0.133 Hz and 0.9 Hz as a respiratory signal of human according to the difference between the frequencies of the respiratory signal and the heartbeat signal. Alternatively, the waveform patterns of the respiratory signal and the ECG signal are different, so the feature can be used to identify the respiratory signal and the ECG signal.

The embodiments of the present invention is applicable to health-care facilities, for example, household infants and young children physiological monitoring device, department of obstetrics and gynecology newborn physiological monitoring system, aged people physiological monitoring system, physiological signal detecting system for obstructive sleep apnea syndrome, and household sleep quality analyzer.

In view of the above, the embodiments provide a highly integrated textile technique, which forms a textile structure capable of measuring the respiratory signal and the ECG signal by using a layout of a conductive textile. Furthermore, the conductive textile can be in a line-like or a surface-like layout.

According to the embodiments of the present invention, the textile structures can be combined with clothes, such that the persons under test can wear the clothes, which is convenient for the movement and the measurement at any time.

Furthermore, the embodiments of the present invention can be combined with a communication device (such as a wireless communication device, and a PDA having wireless communication function). Accordingly, the detected body surface electrical signal of human can be sent to a remote receiving end (such as a physician or a hospital) through the communication device, so as to facilitate the statistics of data.

Furthermore, the embodiments of the present invention can also be combined with an automobile ambulance platform (such as an ambulance) or remote medical platform. Accordingly, the patient can get medical treatment before arriving at the hospital, and the hospital/physician can get to know the body surface electrical signals of the patient as soon as possible, which are helpful for diagnosis.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A textile structure for detecting body surface electrical signals of human, comprising:
 a non-conductive textile, for covering a human body;
 a first conductive textile, coupled to the non-conductive textile, and at least comprising a first region, a second region, and a third region;
 a first test terminal, coupled to the first region of the first conductive textile;
 a second test terminal, coupled to the second region of the first conductive textile;
 a third test terminal, coupled to the third region of the first conductive textile; and
 a second conductive textile, coupled to the non-conductive textile, and connected to the first region and the second region the first conductive textile;
 wherein a conductivity of the first conductive textile is much higher than that of the second conductive textile, the first and the second test terminals are used for detecting an ECG signal, and the first and the third test terminals are used for detecting a respiratory signal.

2. The textile structure according to claim 1, wherein at least one of the first, the second, and the third test terminals comprises a metal male-female buckle.

3. The textile structure according to claim 1, wherein at least one of the first, the second, and the third test terminals comprises a hollow terminal.

4. The textile structure according to claim 1, wherein at least one of the first, the second, and the third test terminals comprises a conductive glue.

5. A signal detector, comprising:
 a textile structure, comprising:
 a non-conductive textile, for covering a human body;
 a first conductive textile, coupled to the non-conductive textile, and at least comprising a first region, a second region, and a third region;
 a first test terminal, coupled to the first region of the first conductive textile;

a second test terminal, coupled to the second region of the first conductive textile;

a third test terminal, coupled to the third region of the first conductive textile; and a second conductive textile, coupled to the non-conductive textile, connected to the first region and the second region of the first conductive textile; wherein a conductivity of the first conductive textile is much higher than that of the second conductive textile, the first, the second, and the third test terminals are used for detecting a body surface electrical signal of human;

a signal acquiring and processing unit, coupled to the first, the second, and the third test terminals, for acquiring and processing the body surface electrical signal; and a filter circuit, coupled to the signal acquiring and processing unit, for separating an ECG signal and a respiratory signal from the body surface electrical signal processed by the signal acquiring and processing unit.

6. The signal detector according to claim 5, wherein at least one of the first, the second, and the third test terminals comprises a metal male-female buckle.

7. The signal detector according to claim 5, wherein at least one of the first, the second, and the third test terminals comprises a hollow terminal.

8. The signal detector according to claim 5, wherein at least one of the first, the second, and the third test terminals comprises a conductive glue.

* * * * *